(12) United States Patent
Lent et al.

(10) Patent No.: US 12,402,777 B2
(45) Date of Patent: *Sep. 2, 2025

(54) MEDICAL IMAGING DEVICE

(71) Applicant: Boston Scientific Scimed, Inc., Maple Grove, MN (US)

(72) Inventors: Eric Lent, Roberts, WI (US); Niraj Rauniyar, Plymouth, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1 day.

This patent is subject to a terminal disclaimer.

(21) Appl. No.: 18/396,860

(22) Filed: Dec. 27, 2023

(65) Prior Publication Data

US 2024/0122451 A1    Apr. 18, 2024

Related U.S. Application Data

(63) Continuation of application No. 17/448,088, filed on Sep. 20, 2021, now Pat. No. 11,896,199.
(Continued)

(51) Int. Cl.
*A61B 1/00* (2006.01)
*A61B 1/06* (2006.01)

(52) U.S. Cl.
CPC ........ *A61B 1/0008* (2013.01); *A61B 1/00117* (2013.01); *A61B 1/0676* (2013.01); *A61B 1/0684* (2013.01)

(58) Field of Classification Search
CPC . A61B 1/00006; A61B 1/00094; A61B 1/015; A61B 1/121; A61B 1/126; A61B 1/303; A61B 2017/32008; A61B 2217/005; A61B 2217/007; A61B 1/00039; A61B 1/0004; A61B 1/00042; A61B 1/00097; A61M 1/77; A61M 1/772; A61M 1/777; A61M 3/0216; A61M 3/022; A61M 2205/3334; A61M 2205/3341
See application file for complete search history.

(56) References Cited

U.S. PATENT DOCUMENTS

| 11,153,970 | B1 * | 10/2021 | Smith | H05K 1/189 |
| 2003/0222325 | A1 * | 12/2003 | Jacobsen | A61B 1/05 |
| | | | | 257/434 |

(Continued)

FOREIGN PATENT DOCUMENTS

| CN | 110604535 A | 12/2019 |
| EP | 3016573 A2 | 5/2016 |

OTHER PUBLICATIONS

International Search Report and Written Opinion issued in International Application PCT/US2021/071509 on Dec. 7, 2021 (12 pages).

*Primary Examiner* — Michael J Carey
*Assistant Examiner* — Stephen Floyd London
(74) *Attorney, Agent, or Firm* — Bookoff McAndrews PLLC

(57) ABSTRACT

A medical device comprising a shaft defining a first channel having a distal opening, a printed circuit board (PCB) coupled to a distal end of the shaft to expose the distal opening to an external environment, wherein the PCB includes an imager and at least one light, the imager and the at least one light mounted on a distal facing surface of the PCB, and an optically clear covering, wherein the covering covers the imager and the at least one light.

20 Claims, 9 Drawing Sheets

Related U.S. Application Data

(60) Provisional application No. 63/083,151, filed on Sep. 25, 2020.

(56) References Cited

U.S. PATENT DOCUMENTS

| | | | |
|---|---|---|---|
| 2004/0147807 A1* | 7/2004 | Viebach | A61B 1/00096 |
| | | | 600/129 |
| 2006/0041188 A1 | 2/2006 | Dirusso et al. | |
| 2006/0146172 A1* | 7/2006 | Jacobsen | H04N 23/50 |
| | | | 348/340 |
| 2008/0255416 A1 | 10/2008 | Gilboa | |
| 2013/0131451 A1 | 5/2013 | Dillinger et al. | |
| 2013/0150673 A1 | 6/2013 | Kakehashi | |
| 2015/0342530 A1 | 12/2015 | Dekker et al. | |
| 2017/0238903 A1 | 8/2017 | Wood et al. | |
| 2017/0325671 A1 | 11/2017 | Hopkins | |
| 2019/0038868 A1 | 2/2019 | Elia et al. | |
| 2019/0070390 A1* | 3/2019 | Isaacson | A61B 5/14503 |
| 2019/0208143 A1* | 7/2019 | Brooks | A61B 1/00183 |
| 2019/0274522 A1 | 9/2019 | Maiorano et al. | |
| 2019/0357973 A1* | 11/2019 | Beeckler | A61B 18/1492 |
| 2020/0194951 A1 | 6/2020 | Loo et al. | |
| 2020/0221598 A1* | 7/2020 | Loo | H05K 1/115 |
| 2021/0290041 A1* | 9/2021 | Morita | A61B 1/051 |
| 2021/0401267 A1* | 12/2021 | Kodama | A61B 1/0676 |

* cited by examiner

MEDICAL IMAGING DEVICE

CROSS-REFERENCE TO RELATED APPLICATIONS

This application is a continuation of U.S. application Ser. No. 17/448,088, filed Sep. 20, 2021, which claims the benefit of priority from U.S. Provisional Application No. 63/083,151, filed on Sep. 25, 2020, each of which is incorporated by reference herein in its entirety.

TECHNICAL FIELD

This disclosure relates generally to an imaging device. At least some embodiments of the disclosure relate to a medical imaging device including a printed circuit board (PCB) and an overmold covering a portion of the device.

BACKGROUND

Medical procedures often use an imaging device to view internal portions of the body during the procedure. For example, in an endoscopic procedure, an endoscope having lighting and an imager at a distal end may be used to view portions of the gastrointestinal tract during a procedure. Various components of medical imaging devices are often potted into a distal cap, thereby resulting in overcrowding and interference between said components. Such issues may cause the imaging devices to malfunction and exhibit various field failures. For example, plastic optical fibers, which may serve as light sources for imaging devices, may interfere with the cables of the imaging component, thereby resulting in a compromised image feed. Overcrowding may also cause wear between cables and components, which, in turn, can result in wire corrosion and damage. Thus, the aforementioned issues and resulting effects may cause significant expense to rework or replace the imaging devices.

SUMMARY OF THE DISCLOSURE

According to an example, a medical device may comprise a shaft defining a first channel having a distal opening, a printed circuit board (PCB) coupled to a distal end of the shaft to expose the distal opening to an external environment, wherein the PCB includes an imager and at least one light, the imager and the at least one light mounted on a distal facing surface of the PCB, and an optically clear covering, wherein the covering covers the imager and the at least one light. The shaft may further define a second channel having a second distal opening exposed to an external environment. The covering may cover all distally-facing surfaces of the PCB.

In another example, the medical device may further comprise a first cable extending through a second channel of the shaft, wherein the first cable is fixed to the PCB. The medical device may further comprise a second cable extending through a third channel of the shaft, wherein the second cable is fixed to the PCB, wherein the first cable and the second cable are configured to steer a distal portion of the medical device. The first cable and the second cable may be electrically conductive. The first cable may extend through a first cable opening of the PCB and the second cable may extend through a second cable opening of the PCB, wherein the first cable opening and the second cable opening are lined with conductive plating. The first cable and the second cable may be electrically connected to the at least one light.

In another example, the at least one light may include a plurality of lights. The at least one light may include a light emitting diode (LED). The covering may not cover the distal opening of the first channel. The PCB may further include at least one capacitor mounted on a proximal facing surface of the PCB. The PCB may be semi-annular. The covering may cover at least a portion of a distally-facing surface of the shaft. The covering may define an opening in fluid communication with the distal opening of the first channel.

According to another example, a medical device may comprise a shaft defining a first channel and a second channel each extending longitudinally through the shaft and each having a distal opening exposed to an external environment, a printed circuit board (PCB) adjacent a distal end of the shaft, wherein the PCB includes an imager and a light, the imager and the light mounted on a distal facing surface of the PCB, a first cable and a second cable, wherein the first cable and the second cable extend through third and fourth channels of the shaft respectively and are fixed to the PCB, and an optically clear covering that seals the PCB from the external environment. The first channel may extend distally past the PCB, and the second channel may extend distally past the PCB. The covering may cover all distally-facing surfaces of the PCB.

According to another example, a medical device may comprise a shaft, a printed circuit board (PCB) connected to a distal end of the shaft, wherein the PCB includes an imager and a light each mounted on a distal facing surface of the PCB, an optically clear covering that seals the PCB from an external environment, a first cable fixed to the PCB and configured to steer a distal portion of the shaft, and wherein the first cable is electrically conductive and provides current to at least one of the image and the light. The medical device may further comprise a second cable fixed to the PCB and configured to steer the distal portion of the shaft, wherein the PCB further includes a second light mounted on the distal facing surface of the PCB.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

DETAILED DESCRIPTION

Figure 1A:
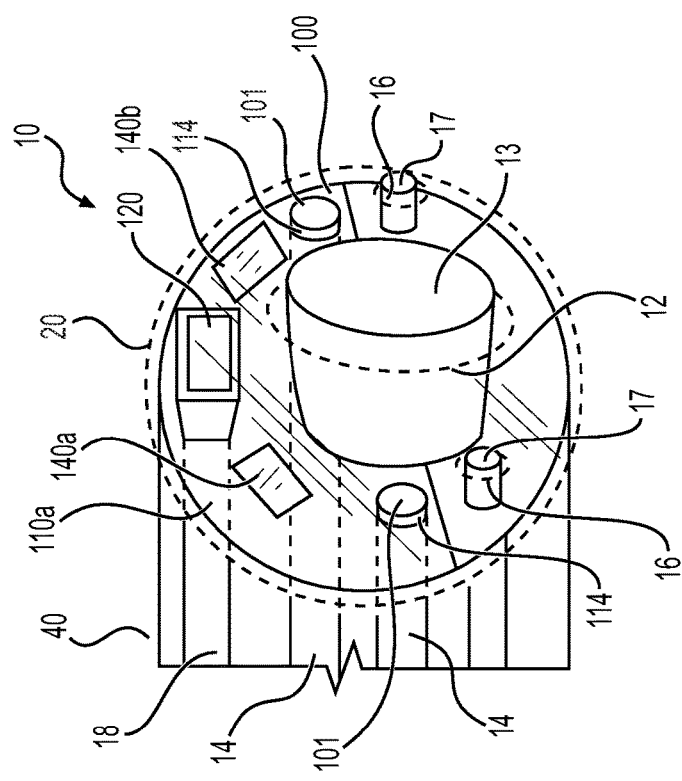
FIG. 1A is a perspective view of a medical device, according to an embodiment.
Figure 1A:
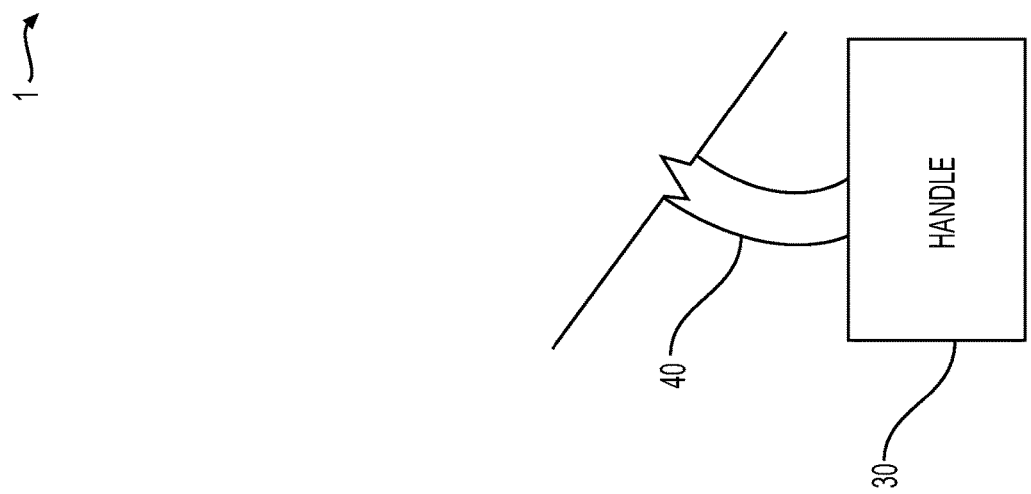

Reference will now be made in detail to aspects of the disclosure, examples of which are illustrated in the accompanying drawings. Wherever possible, the same or similar reference numbers will be used through the drawings to refer to the same or like parts. The term "distal" refers to a portion farthest away from a user when introducing a device into a subject (e.g., a patient). By contrast, the term "proximal" refers to a portion closest to the user when placing the device into the subject.

Both the foregoing general description and the following detailed description are exemplary and explanatory only and are not restrictive of the features, as claimed. As used herein, the terms "comprises," "comprising," "having," "including," or other variations thereof, are intended to cover a non-exclusive inclusion such that a process, method, article, or apparatus that comprises a list of elements does not include only those elements, but may include other elements not expressly listed or inherent to such a process, method, article, or apparatus. In this disclosure, relative terms, such as, for example, "about," "substantially," "generally," and "approximately," are used to indicate a possible variation of ±10% in a stated value or characteristic.

Embodiments of the disclosure may solve one or more of the limitations in the art. The scope of the disclosure, however, is defined by the attached claims and not the ability to solve a specific problem. The disclosure is drawn to a medical device including an imager, a printed circuit board (PCB) in a distal portion of the imaging device, and an overmold covering a distal portion of the medical device. The medical device can be, as an example, any imaging scope (e.g., bronchoscope, duodenoscope, endoscope, colonoscope, ureteroscope, etc.), catheter, tool, instrument, or the like, having a shaft that extends distally from a handle to a distal portion of the device. In some embodiments, the shaft may be a multi-lumen extrusion including a plurality of separate channels, e.g., for fluid, cables, and for tools in working channels. Thus, the shaft may function as a sheath for the various tubings or channels. The number of lumens of a multi-lumen extrusion is not particularly limited. The working channel, likewise, may extend distally from a handle within a lumen of said shaft. The working channel may be a channel of the multi-lumen extrusion or may be a tubing of any suitable material within a channel, and the working channel is configured to receive at least one accessory device. In some instances, the tubing may extend distally past a distal end of the shaft.

The PCB is not particularly limited and may be any suitable board configured to be populated with electrical components. For example, the PCB may be any standard 1-sided or 2-sided PCB, and the PCB may be populated with components by any suitable means, e.g., Surface Mount Technology (SMT). In another example, the PCB may include Multilayer Ceramic Chip Capacitor (MLCC) characteristics, which allow capacitors or other electrical components to be embedded into the PCB. In other examples, the PCB may further include solder pads, or any other similar means, to allow wires to be soldered to the PCB. The PCB may be of any suitable shape, e.g., round, and size, e.g., 2 mm-3.4 mm in thickness, that allows the PCB to be overmolded (as further discussed below). Electrical components fixed onto one or both sides of the PCB may include any suitable imaging component, light source component, capacitor, sensor, accelerometer, probe, laser, and any other appropriate visualization, lighting, or diagnostic or therapy components.

The PCB may be placed within the distal end of the shaft, positioned adjacent to the distal end of the shaft, or may be distal relative to the distal end of the shaft. The PCB may include openings and/or a shape or curvature to accommodate for, or otherwise be aligned with, the tubings, channels, or cables extending within the shaft. The openings may be of any suitable size or shape to allow for the tubings or channels of the shaft to be in alignment with or otherwise in fluid communication with, the openings. In some instances, the openings may be of any suitable size or shape to allow for the tubings or channels to extend distally past the PCB.

The manner in which the PCB is fixed to the distal end of the shaft is not particularly limited. For example, an outer surface of the shaft, e.g., the distal facing surface of the shaft, may be epoxied or tacked onto the PCB by any suitable means. Furthermore, cables, e.g., steering cables, of the device may be soldered onto a surface, e.g., the distal facing surface, of the PCB, thereby providing further securing. A fixture, e.g., molded silicone or optically clear epoxy, may also be implemented to assist this process of fixing the PCB onto the distal portion of the medical device.

The overmold may cover and adhere to a distal portion of the medical device. This may include a portion of the distal tip of the device, the PCB, and a distal portion of the shaft. The material of the overmold is not particularly limited, and may be any suitable biocompatible material. For example, the overmold may be of an optically clear material or epoxy. The overmold may sufficiently adhere onto the distal portion of the medical device to withstand typical wear and friction while traversing various bodily lumens. As noted in the aforementioned examples of materials, the overmold may be an optically clear material, so that imaging components continue to provide a clear image feed through the overmold layer, and light components effectively illuminate past the layer. Furthermore, the overmold may be shaped or molded in such a manner to accommodate for an imager fixed at any angle relative to an axis of the shaft, working channel, and/or PCB.

The overmold layer generally does not cover the portion of the distal facing surface of the shaft including the one or more working and fluid channels and/or tubings. However, in certain instances, the overmold layer may further include openings at the distal tip aligned with the fluid channels and/or working channels, and allow passage of fluid or instruments therethrough. Furthermore, in some embodiments, the overmold may also include an opening for an imaging component. The overmold may be flush against the outer surfaces of the tubings and/or channels, thereby sealing the remaining distal portion of the device from the external environment. The overmold may contain the electronics and encase them to seal the electronics from saline and other fluids. Thus, the overmold may effectively seal the PCB and other electronic components from fluid ingress. The overmold, due to some flexibility in its material and structure, may also provide strain relief for the electronic components. In some embodiments, the distal facing surface of the overmold may also have a particular shape. For example, the distal facing surface may have a curved shape that allows an enhanced or focused light dispersion pattern from illumination sources on the PCB. The overmold may also function as a heat sink for the illumination sources on the PCB, conducting heat away from the distal tip of the medical device. The thickness of the overmold is not particularly limited, and may be optimized for shape, light transmission, heat sinking, manufacturability, cost, etc.

The manufacturing process of the above discussed medical device is not particularly limited. The distal portion of the device includes a suitable PCB including various desired electronic components mounted onto said PCB. As noted above, the PCB may be of any suitable shape, e.g., a half-annular shape. The PCB may then be fitted onto the distal end of the shaft, e.g., MLE, via any suitable manner. For example, a PCB may be adhered or tacked onto the distal facing surface of the MLE. Prior to said tacking, the MLE may be trimmed or shaped to better accommodate for the PCB, so that the distal facing surface of the PCB and of the shaft are aligned/planar. In another example, the shaft may have lips or edges slightly extruding beyond the distal face of the shaft, and the PCB may be fitted within the lips or edges. Cables, e.g., steering cables extending within lumens of the shaft, may be fixed, e.g., soldered, onto the PCB, thereby further securing the PCB onto the medical device. After coupling the PCB onto the shaft via any suitable manner, at least the distal portion of the device may be placed or fitted within a molded fixture, e.g., a molded silicon fixture. The molded fixture may be shaped so that only a desired area for overmolding may be exposed to an injection molding of the overmold material. The overmold may be dispensed around said desired area, and afterwards, may be subjected to a series of curing and/or baking procedures to harden the overmold. In instances in which an overmold is to be applied over an entire distal face of the device, rods may be inserted within openings of channels and/or tubes. The rods may be removed after application of the overmold to form openings for the passage of instruments and/or fluid therethrough.

Referring to FIG. 1A, a medical device 1, e.g., an imaging scope, according to an embodiment is shown. Medical device 1 includes a shaft 40 (e.g., a catheter) and a handle 30 coupled to a proximal portion of shaft 40. Handle 30 is not particularly limited, and may be any suitable imaging device handle. For example, handle 30 may include at least one aspect for actuating or controlling medical device 1 and any tools or devices associated with medical device 1. Shaft 40 may extend from handle 30 to a distal portion 10 of medical device 1. As discussed above, shaft 40 may be any suitable biocompatible and flexible shaft. As shown in FIG. 1, shaft 40 may be a multi-lumen extrusion including a plurality of lumens to accommodate for various separate channels or cables, e.g., an electrical cable 18, irrigation/aspiration tubes 16, cables 14, and a working channel 12.

Electrical cable 18 may be any suitable cabling receiving and sheathing at least one electrical wire (not shown) from the electrical component(s) mounted onto a PCB 100 (discussed in further detail below). Thus, cable 18 may extend distally from handle 30 or an external electrical source (positive, ground, and/or negative voltage) to the electrical components, e.g., an imager 120 and light sources 140*a*, 140*b*, of PCB 100. Cable 18 may be of an insulative material, and may include at least one lumen (not shown) for receiving the at least one wire. There may be separate wires for each of imager 120, light source 140*a*, and light source 140*b*.

Tubes 16 may be any suitable tubing for irrigation or aspiration purposes. For example, tubes 16 may be a saline flush tube. Tubes 16 include channels 17 through which irrigation or aspiration is provided. Tubes 16 may extend distally from handle 30 or an external component, and may extend distally past PCB 100, as shown in FIG. 1A.

Cable 14 may be any suitable cable, e.g., a Bowden cable, configured to help steer distal portion 10 of device 1. There may be any suitable number of cables 14, e.g., one, two, three, or four cables 14 (two are shown in FIG. 1A). A distal end of each cable 14 may fixedly connect to PCB 100 at a corresponding opening 101. A proximal end of each cable 14 may be fixed to an actuator of handle 30, as is known in the art. Actuation of the actuator will push or pull cable(s) 14, causing the distal portion of shaft 40 to articulate in a left, right, up, and/or down direction. Shaft 40 may include an articulation joint at a distal end of shaft 40 that has sufficient flexibility to bend.

Furthermore, one or more of cables 14 may also be configured to draw current from an electrical source to power electrical components on the PCB, e.g., lights 140*a*, 140*b*, which may require a different voltage than other electrical components, e.g., imager 120. Thus, cable 14 may be of any suitable material, and in some instances, may be of a conductive material, e.g., medical grade stainless steel. When configured to carry current, cable 14 may be a 20-50 gauge wire, but is not limited thereto. Moreover, cable 14, when conductive, may further include an insulative sheathing around the conductive cable. As mentioned, cable 14 may extend distally from a portion of handle 30 configured to control the steering of distal portion 10 and/or an electrical source (positive, ground, and/or negative voltage), and the distal end of cable 14 may be fixed onto PCB 100 through cable opening 101 provided on PCB 100. Each cable opening 101 may be plated with a conductive material 114 for electrical connectivity purposes. The fixing of cable 14 to cable opening 101 may be via any suitable means, e.g., soldering or fastening with electrically conductive epoxy.

In FIG. 1A, working channel 12 may be any suitable tubing with at least one lumen 13 extending from a proximal end to a distal end of channel 12. Working channel 12 may be configured to receive at least one accessory device via lumen 13. The size, e.g., diameter, of lumen 13 is not particularly limited, and, for example, may be about 1.20 mm-1.65 mm Channel 12 may extend from handle 30 to a distal portion 10 of device 1, and have an opening at its distal end.

Distal portion 10 of medical device 1 includes PCB 100 and an overmold 20. PCB 100 is semi-circular or semi-annular, and includes a distal facing surface 110*a* (shown in FIGS. 1A and 3A) and a proximal facing surface 110*b* (shown in FIG. 3B) onto which electrical components may be mounted. PCB 100 may have a similar shape as the PCBs shown in FIGS. 4A-4B. PCB 100 may be distal relative to shaft 40, within a distal end of shaft 40, or adjacent to a distal end of shaft 40. As shown in FIG. 1A, PCB 100 is adjacent to a distal end of shaft 40, and is fixed to said distal end via an adhesive or epoxy. The semi-annular shape of PCB 100 has a radially-inward curved edge to accommodate for channel 12. Moreover, PCB 100 includes a number of openings 101 for receiving cables 14. PCB 100 is described in further detail below, when referring to FIGS. 3A-3D.

Figure 2:
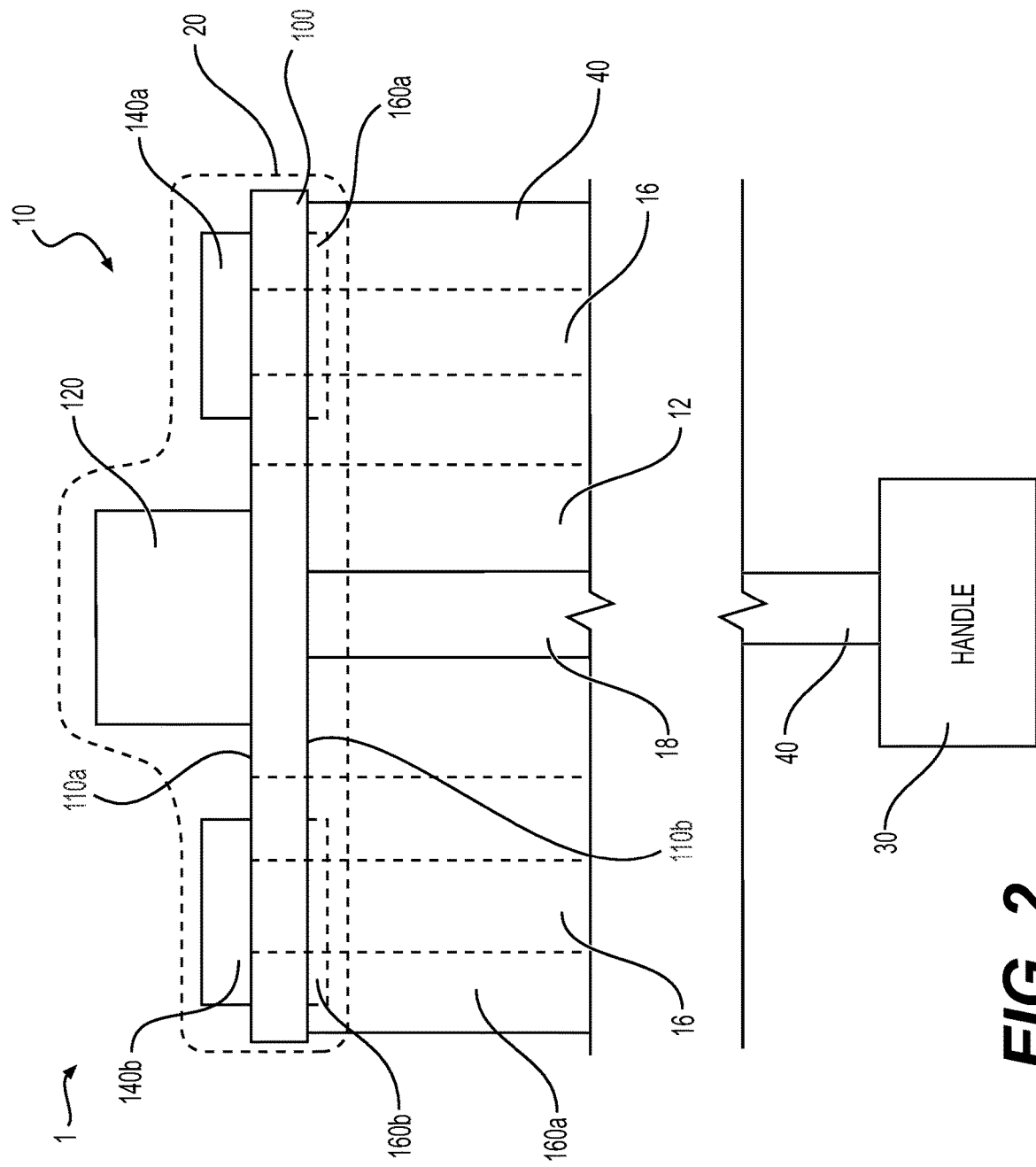
FIG. 2 is a partial cross-sectional side view of a portion of the medical device of FIG. 1.

Overmold 20 is a biocompatible layer or substrate that covers a portion of distal portion 10. Said portions include at least a portion, or all, of PCB 100. Overmold 20 adheres onto a distal portion of shaft 40 and may cover all portions of PCB 100 and the electronic components mounted thereon (e.g., imager 120, light sources 140*a*, 140*b*, and capacitors 160*a*, 160*b*) that are exposed to an external environment. Overmold 20 thereby serves as a seal from any fluid ingress. It is noted that, in other embodiments, overmold 20 may not extend proximally past PCB 100 to the distal portion of shaft 40. However, such adhesion to shaft 40 may further help maintain PCB 100 adjacent against the distal end of shaft 40 and better act as a seal. Overmold 20 is optically clear to allow maximum illumination transmission from light 140*a*, 140*b* across wavelengths of interest. Furthermore, the distally facing portion of overmold 20 may be curved to accommodate for the protrusions of imager 120 and light sources 140*a*, 140*b*. As noted above, overmold 20 may be curved or shaped to accommodate for imager 120 fixed at an angle relative to PCB 100, and also an enhanced or focused light dispersion pattern from light sources 140*a*, 140*b*. It is noted that the distal openings of channel 12, and tubes 16 are not covered by overmold 20. FIG. 2 illustrates a side profile of distal portion 10, and the positioning of overmold 20 around and over distal portion 10, including overmold 20 adhering onto a distal portion of shaft 40. Thus, overmold 20 may cover all distally facing surfaces of PCB 100, while not covering the distal openings of channel 12 and tube 16.

Figure 1B:
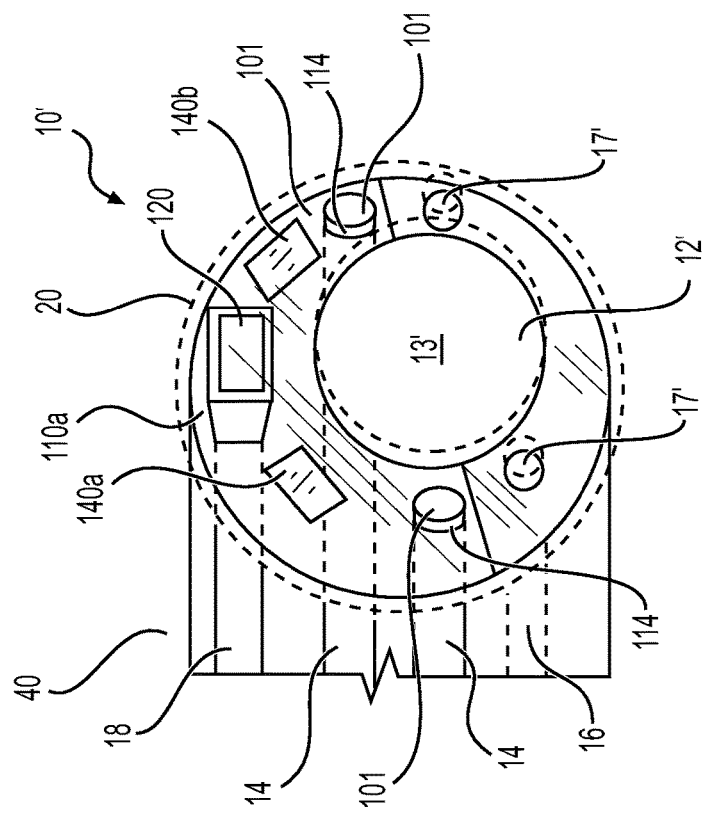
FIG. 1B is a perspective view of a medical device, according to another embodiment.
Figure 1B:
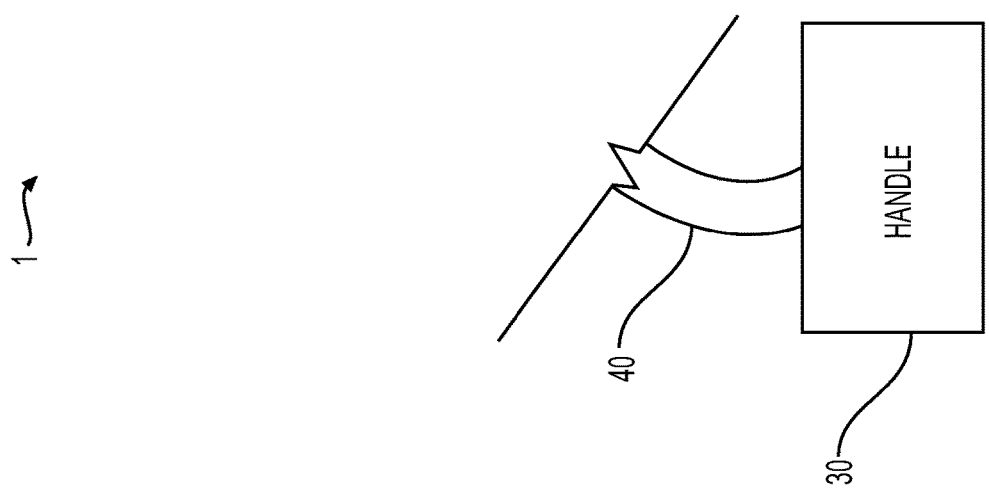

Referring to FIG. 1B, another embodiment of distal portion 10' of device 1 is shown. Like reference numerals refer to like parts. Distal portion 10' is without separate tubes (e.g., tube 12 and tubes 16) extending within the plurality of lumens of shaft 40, as shown in FIG. 1A. Rather the lumens of shaft 40 define working channel 12', and aspiration/irrigation channels 17'. Channel 12' may define lumen 13' extending from a proximal end to a distal end of channel 12'. Thus, channel 12' and channels 17' may have distal openings at the distal end of shaft 40.

Figure 3A:
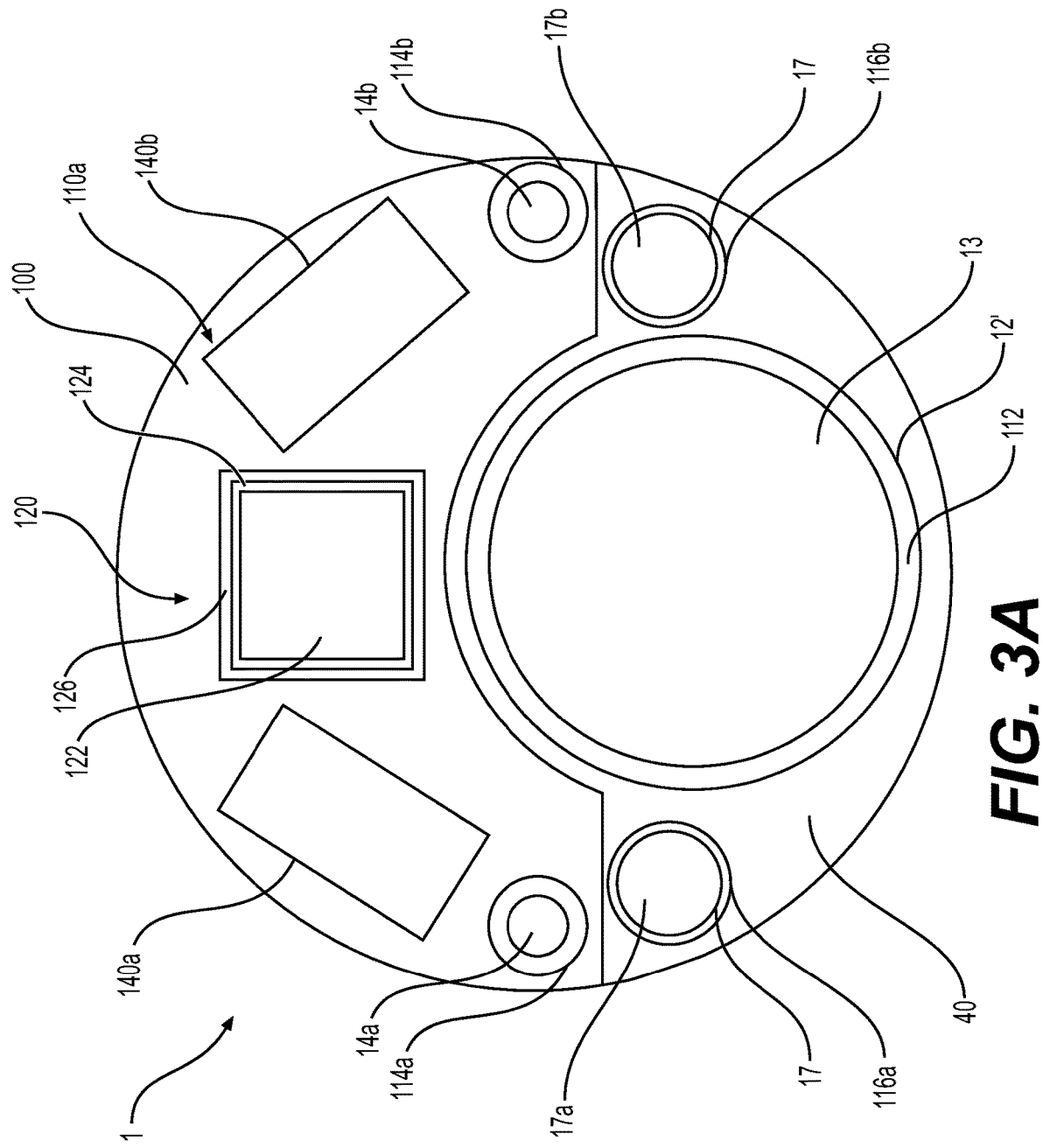
FIG. 3A is a view of a distal end of the medical device of FIG. 1.

FIG. 3A illustrates a distal end of device 1, including distal facing surface 110*a* of PCB 100 and a distal facing surface of shaft 40. As discussed above, cables 14 may be received by cable openings 101 (not shown) lined with conductive material 114. Cables 14 may be soldered or epoxied onto distal surface 110*a* of PCB 100. Channel 12 and tubes 16 extend distally past PCB 100. However, as noted above, in some embodiments, e.g., device 1', the lumens of shaft 40 may define a working channel and irrigation channels. Thus, in such embodiments, the distal ends of the channels are the distal end of shaft 40. Accessory instruments may extend distally through lumen 13, and fluid and suction may be dispensed from irrigation/aspiration channels 17 through distal openings 17*a*, 17*b*.

As shown in FIG. 3A, distal facing surface 110*a* of PCB 100 is populated with imager 120 and lights 140*a*, 140*b*, which are mounted onto surface 110*a*. Imager 120 includes a lens 122, a blocking layer 124, and a casing 126. Lens 122 is not particularly limited and may be any suitable imaging lens or lens stack. Blocking layer 124 may be a paint, an epoxy, or a similar material applied to the side surfaces of imager 120. Layer 124 may help block light from lights 140*a*, 140*b* from entering imager 120 except light entering through lens 122, and reduce haze or bright spots in the imaging feed from imager 120. It is noted that layer 124 may be applied to any number of the side surfaces of imager 120. Casing 126 may be any suitable housing for containing all of the components of imager 120. In other embodiments, imager 120 may be without layer 124, and only include casing 126. In some other embodiments, imager 120 may be without casing 126, and only include layer 124, or may include layer 124 on the outside of casing 126. In other embodiments, imager 120 may further include a cover plate (not shown) on top of the distal facing surface of lens 122. The cover plate may be of any suitable material that does not affect image quality, e.g., glass or plastic, and may serve as a protective barrier of lens 122. It is noted that such a cover plate may be implemented when overmold 20 (shown in FIG. 2) does not cover imager 120, and instead includes an opening that seals around imager 120. In other embodiments, imager 120 can include a cover, and overmold 20 can be formed over the cover.

Lights 140*a*, 140*b* may be any suitable source of illumination, e.g., LED. The emitted light from lights 140*a*, 140*b* may be of any suitable wavelength, e.g., white light, infrared, etc. As shown in FIG. 3A, lights 140*a*, 140*b* are on opposite sides of imager 120. However, it is noted that the arrangement or positioning of imager 120 and lights 140*a*, 140*b* is not particularly limited, and may be any suitable arrangement. Distal facing surface 110*a* may further include other various components such as solder pads and connectors which may improve assembly and connectivity.

Figure 3B:
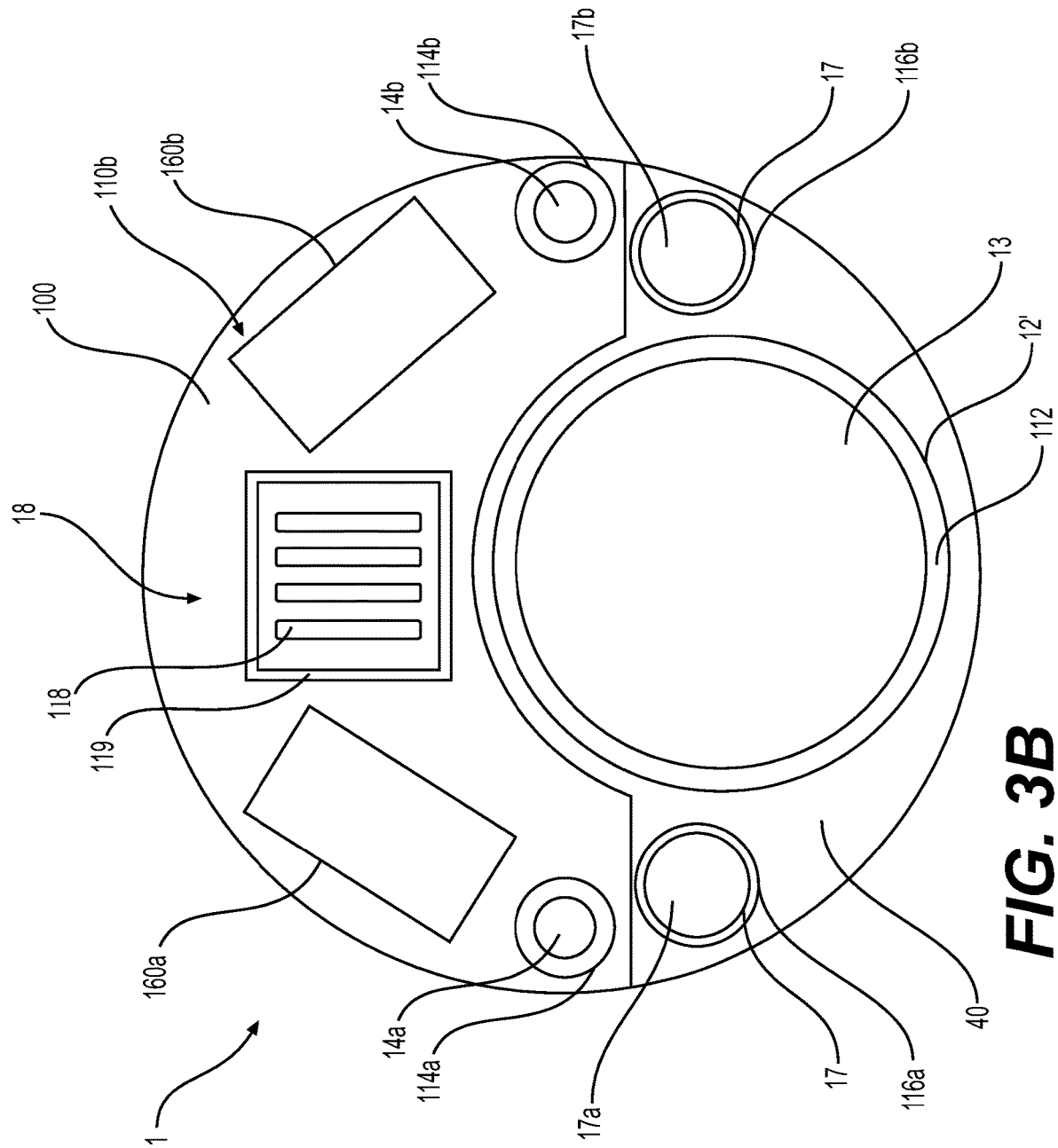
FIG. 3B is a cross-sectional view of a portion of the medical device of FIG. 1, showing a proximally-facing surface of a PCB.

FIG. 3B illustrates a proximal surface 110*b* of PCB 100 and a portion of shaft 40, taken as a cross-section of device 1. Like reference numerals refer to like parts. Proximal facing surface 110*b* is populated with capacitors 160*a*, 160*b*. Capacitors 160*a*, 160*b* may be any suitable capacitors, e.g., decoupling capacitors. In some embodiments, one terminal (not shown) of capacitors 160*a*, 160*b* may provide a voltage connection to imager 120 while the other terminal (not shown) of capacitor 160*a*, 160*b* provides a ground connection to imager 120. Thus, capacitors 160*a*, 160*b* may hold charge to help the voltage of imager 120 to stay steady, which in turn helps image quality from imager 120. Capacitors 160*a*, 160*b* may be any suitable size and thickness. Capacitors 160*a*, 160*b* may be of a negligible thickness so that proximal surface 110*b* of PCB 100 may be adjacent to a distal surface of shaft 40. It is further noted that the arrangement or positioning of capacitors 160*a*, 160*b* is not particularly limited, and may be different from what is shown in FIG. 3B. Moreover, the number of capacitors, e.g., one, two, three, etc., is not particularly limited as well.

Proximal facing surface 110*b* is further populated with electrical cable 18. Proximal facing surface 110*b* may further include solder pads 118, which may be fabricated as part of PCB 100. Solder pads 118 may be soldered to various electrical wires of cable 18, which may electrically connect to the various components, e.g., imager 120, lights 140*a*, 140*b* (not shown).

Figure 3C:
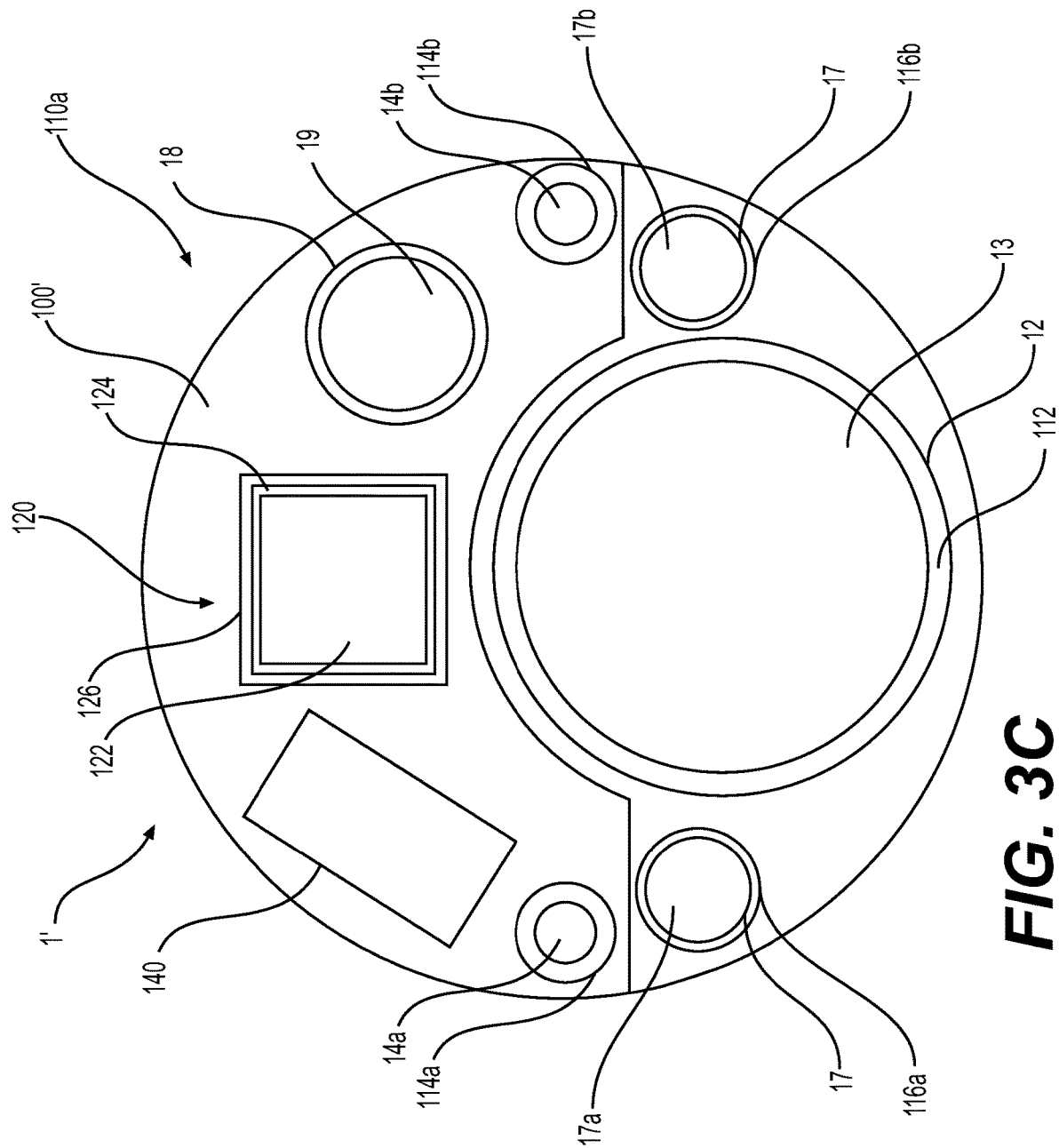
FIG. 3C is a view of a distal end of a medical device of another embodiment.
Figure 3D:
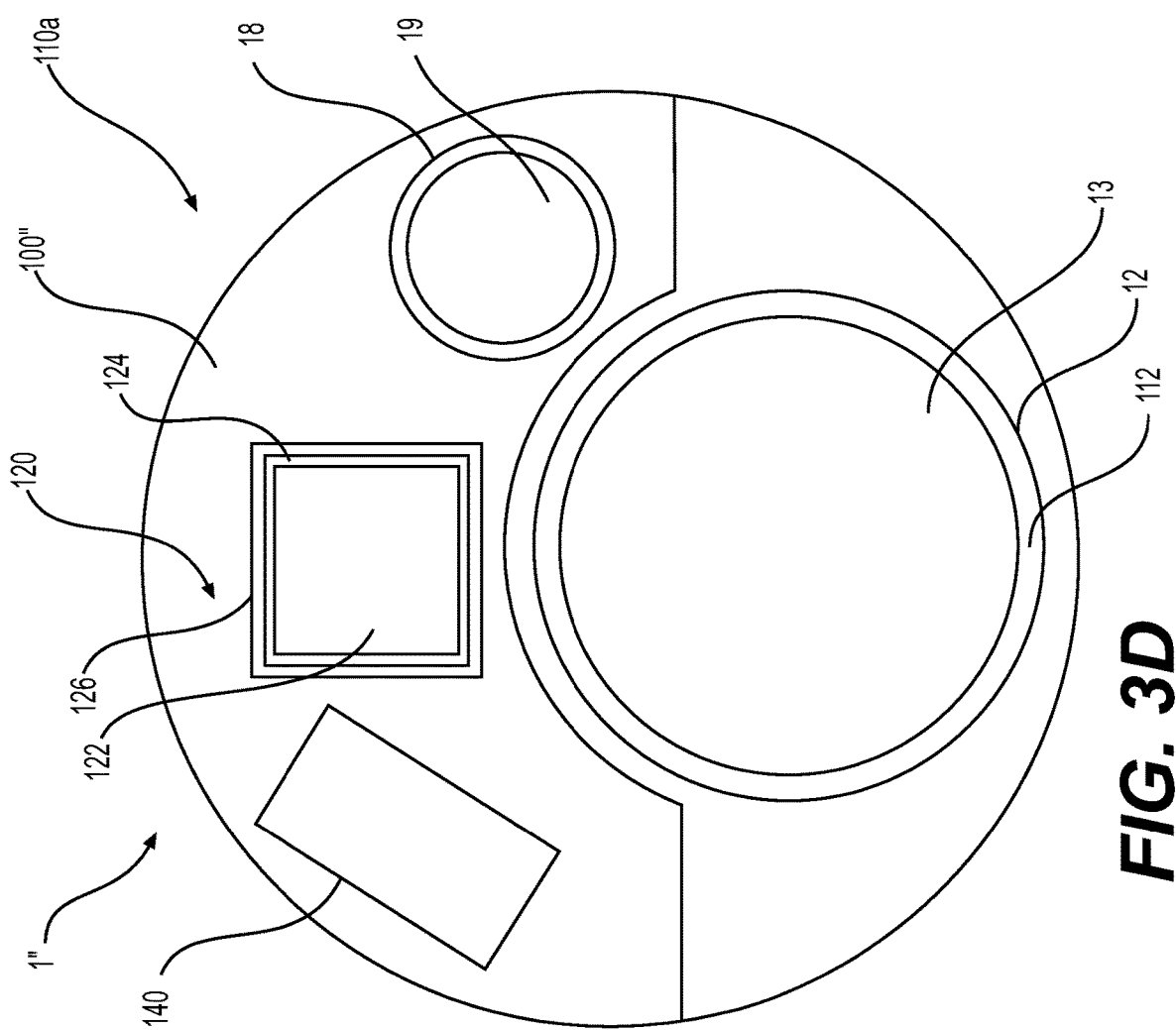
FIG. 3D is a view of a distal end of a medical device of another embodiment.

PCB 100 is not limited to the various electronic components, configurations, and sizes discussed above, referring to FIGS. 3A and 3B. FIGS. 3C and 3D illustrate additional PCB embodiments (100', 100") including different components and layouts. Like reference numerals refer to like parts. As shown in FIG. 3C, PCB 100' includes one light 140, and further includes a second channel 18. Second channel 18 includes a lumen 19. The size, e.g., diameter, of lumen 19 is not particularly limited. An additional accessory instrument/device may extend distally through lumen 19. The additional accessory device is not particularly limited, and may include, for example, a laser probe, an electrohydraulic lithotripsy (EHL) probe, a spectrometer, an electromagnetic sensor, or an ultrasound sensor. The presence of second channel 18 may allow a physician to access and use both a primary instrument, e.g., forceps or retrieval device, and the additional accessory instrument at the same time.

As shown in FIG. 3D, PCB 100" may also be without some of the electrical components discussed above. PCB 100" is without tubes 16 and cables 14 (shown in FIGS. 3A and 3C). Thus, PCB 100", and shaft 40, may be of a smaller diameter, which may be preferred by physicians in certain instances. FIGS. 3C and 3D illustrate the customizable nature of a printed circuit board (e.g., PCB 100', 100"), and how the board may be tailored to suit various purposes and needs of physicians.

Figure 4A:
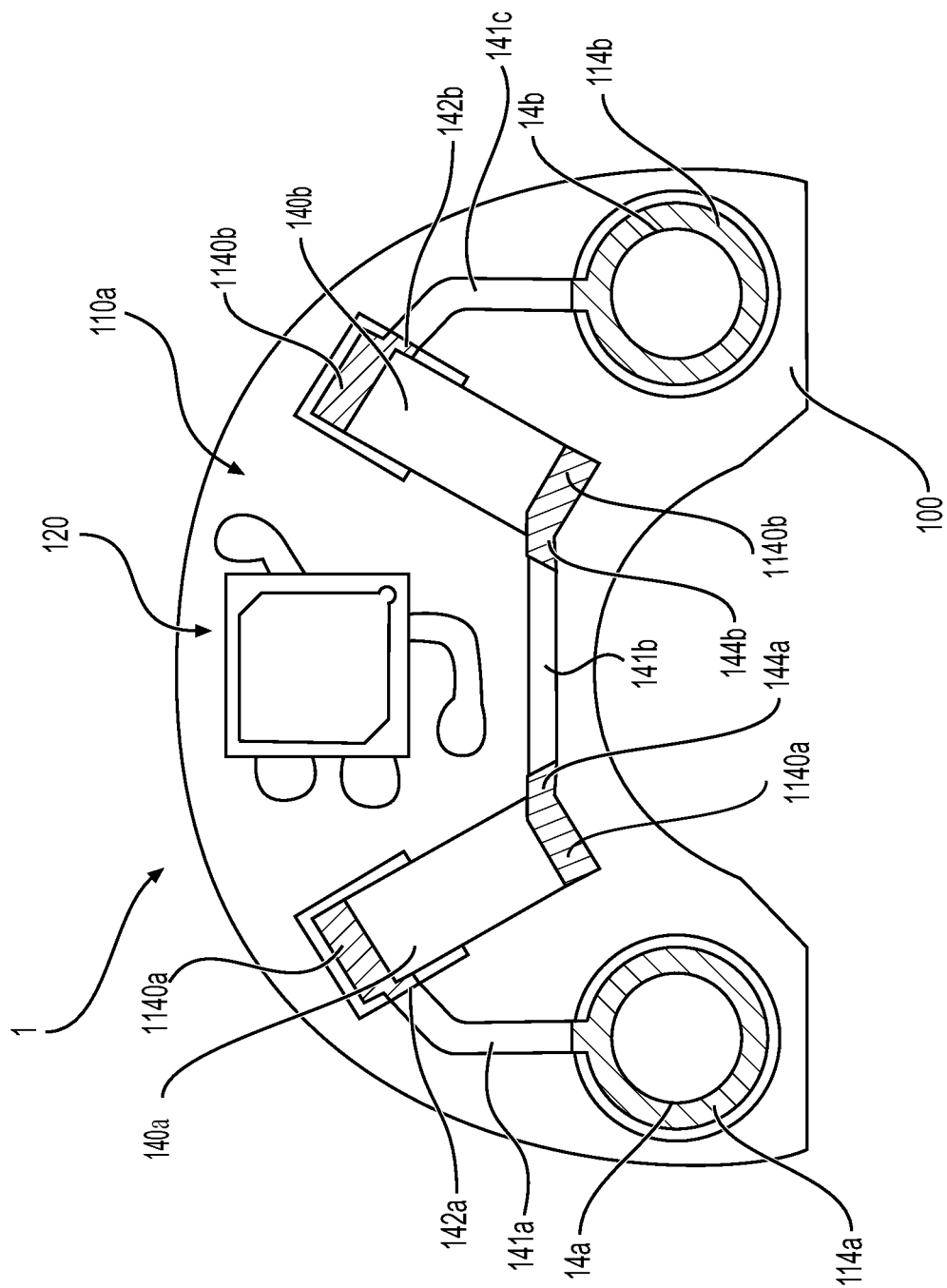
FIG. 4A is a view of a distal surface of a PCB according to an embodiment.
Figure 4B:
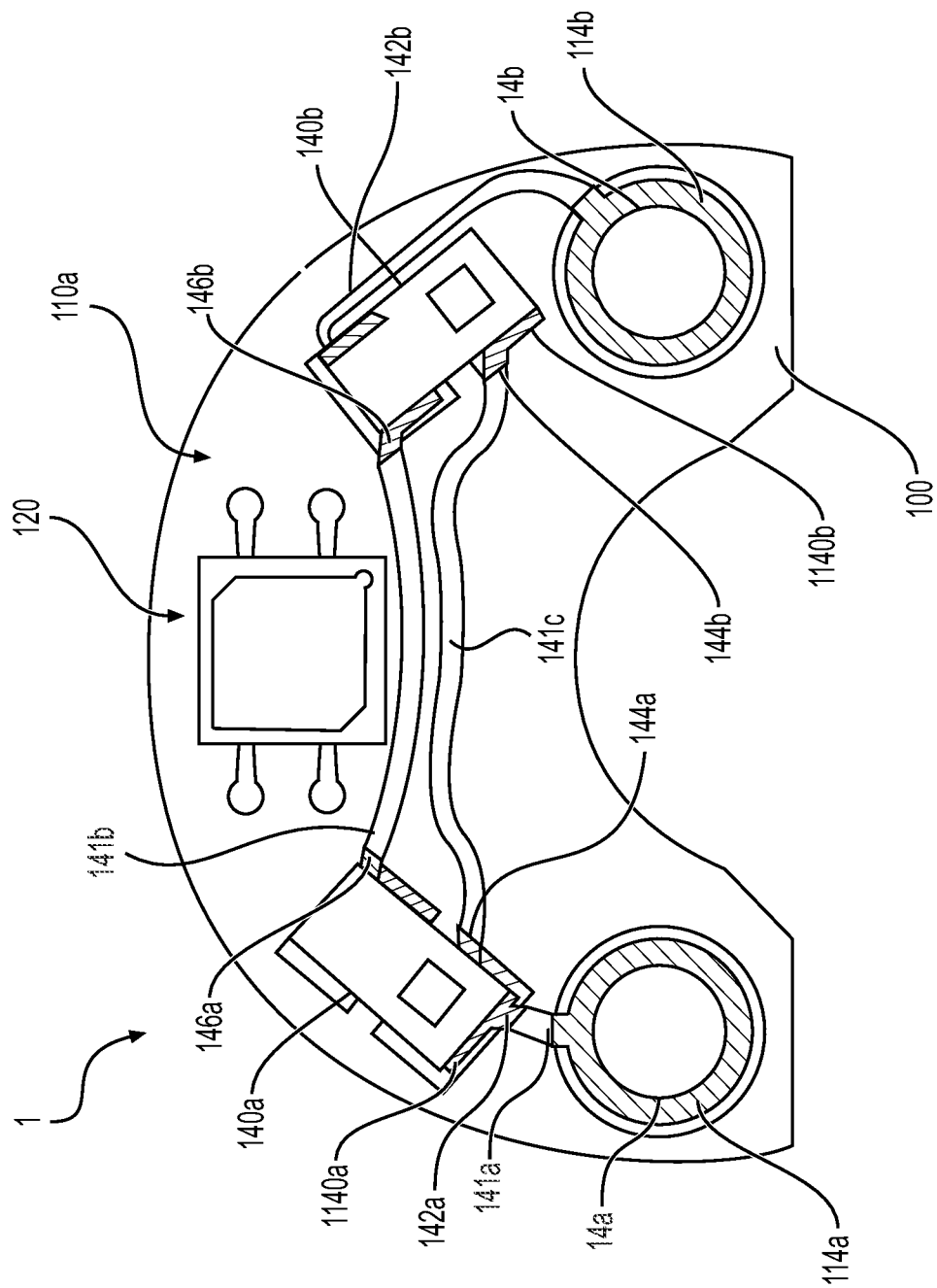
FIG. 4B is a view of a distal surface of a PCB according to another embodiment.

FIGS. 4A and 4B illustrate distal facing surface 110*a* of PCB 100. Like reference numerals refer to like parts. Moreover, FIGS. 4A and 4B illustrate the electrical connection between cables 14 (now differentiated by 14*a*, 14*b*), when electrically conductive, and lights 140*a*, 140*b*. As discussed above, cables 14*a*, 14*b* may be soldered or epoxied onto PCB 100 through cable openings 101 (not shown), which include conductive plating 114*a*, 114*b*. Conductive platings 114*a*, 114*b* outline the circumference of the cable openings, thereby surrounding cables 14*a*, 14*b*. The current drawn by cables 14a, 14b may be received by plating 114a, 114b, which in turn route the current towards lights 140a, 140b.

FIG. 4A illustrates an example of a serial PCB routing between cable 14a, lights 140a, 140b, and cable 14b. As shown, cable 14a is connected to conductive plating 114a, which is connected to light 140a via a first conductive trace 141a extending to a first connection point, e.g., a terminal, 142a. Light 140a also includes a second connection point 144a. Second connection point 144a connects to light 140b via a second conductive trace 141b extending to a second connection point 144b of light 140b. A first connection point 142b of light 140b is connected to conductive plating 114b via a third conductive trace 141c, which connects to cable 14b. It is noted that each of the aforementioned first and second connection points 142a, 144a, 142b, and 144b of lights 140a, 140b are lined with a conductive plating 1140a, 1140b for connectivity purposes. For example, conductive plating 1140a, 1140b may be fabricated in PCB 100 for the aforementioned connections points of lights 140a, 140b. In this embodiment, plating 1140b may serve as a voltage supply, while plating 1140a serves as the electrical ground. For example, cable 14b may apply 6 V to plating 1140b, which would result in both lights 140a, 140b being supplied 3 V, due to the serial routing.

FIG. 4B illustrates an example of a parallel PCB routing between cable 14a, lights 140a, 140b, and cable 14b. As shown, cable 14a is connected to conductive plating 1140a, which is connected to light 140a via first conductive trace 141a extending to first connection point 142a. Light 140a also includes second connection point 144a and a third connection point 146a. There is a parallel connection between light 140a and light 140b, as second connection point 144a and third connection point 146a respectively connect with second connection point 144b and a third connection point 146b of light 140b via conductive traces 141b, 141c respectively. It is noted that each of the aforementioned first, second, and third connection points 142a, 144a, 146a, 142b, 144b, and 146b of lights 140a, 140b are lined with a conductive plating 1140a, 1140b for connectivity purposes. For example, conductive plating 1140a, 1140b may be fabricated in PCB 100 for the aforementioned connections points of lights 140a, 140b. In this embodiment, plating 1140b may serve as a voltage supply, while plating 1140a serves as the electrical ground. For example, cable 14b may apply 3 V to plating 114b, which would result in both lights 140a, 140b being supplied 3 V, due to the parallel routing.

It is noted that cables 14a, 14b are not limited to electrically powering lights 140a, 140b, and may provide current to other various electric components of PCB 100. Cables 14a, 14b may power two separate device voltages if provided with an additional electrical ground, or provide a single device voltage supply and ground.

It will be apparent to those skilled in the art that various modifications and variations can be made to the disclosed device without departing from the scope of the disclosure. Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A medical device, comprising:
    a shaft having a distal facing surface at a distal end of the shaft and defining a channel having a distal opening; and
    a printed circuit board (PCB) coupled to the distal end of the shaft and having a concavity to expose the distal opening of the channel to an external environment, wherein the PCB includes an electrical component mounted on a distal facing surface of the PCB;
    wherein the distal facing surface of the shaft and the distal facing surface of the PCB are flush.

2. The medical device of claim 1, wherein the electrical component includes an imager and at least one light.

3. The medical device of claim 2, further comprising an optically clear covering, wherein the covering covers the imager and the at least one light, and wherein the covering contacts a distal facing surface of the imager and a distal facing surface of the at least one light.

4. The medical device of claim 3, wherein the optically clear covering covers at least a portion of the distal facing surface of the PCB, wherein the covering does not cover the distal opening of the channel, and wherein the covering defines an opening in fluid communication with the distal opening of the channel.

5. The medical device of claim 1, wherein the PCB further includes at least one capacitor mounted on a proximal facing surface of the PCB.

6. The medical device of claim 1, wherein the shaft further defines a second channel having a second distal opening exposed to the external environment.

7. The medical device of claim 1, wherein the medical device further comprises a first cable extending through a second channel of the shaft, wherein the first cable is fixed to the PCB.

8. The medical device of claim 7, wherein the medical device further comprises a second cable extending through a third channel of the shaft, wherein the second cable is fixed to the PCB, and wherein the first cable and the second cable are configured to steer a distal portion of the medical device.

9. The medical device of claim 8, wherein the first cable and the second cable are electrically conductive, wherein the first cable extends to a first cable opening of the PCB and the second cable extends to a second cable opening of the PCB, wherein the first cable opening and the second cable opening are lined with conductive plating.

10. The medical device of claim 9, wherein the first cable and the second cable are electrically connected to a plurality light emitting diodes (LED).

11. A medical device, comprising:
    a shaft having a distal facing surface at a distal end of the shaft, the shaft further defining a channel extending longitudinally through the shaft and having a distal opening exposed to an external environment;
    a printed circuit board (PCB) adjacent the distal end of the shaft, wherein the PCB includes an electrical component mounted on a distal facing surface of the PCB; and
    a cable, wherein the cable extends through the channel of the shaft and is fixed to the PCB;
    wherein the distal facing surface of the shaft and the distal facing surface of the PCB are flush.

12. The medical device of claim 11, wherein the channel is a first channel, and wherein a second channel extends longitudinally through the shaft and has a distal opening exposed to the external environment.

13. The medical device of claim 12, wherein the cable is a first cable and the medical device further comprises a second cable, wherein the first cable and the second cable extend through the first and the second channels of the shaft respectively and are fixed to the PCB.

14. A medical device, comprising:
a shaft having a distal facing surface at a distal end of the shaft;
a printed circuit board (PCB) connected to the distal end of the shaft, wherein a distal facing surface of the PCB and the distal facing surface of the shaft are flush; and
a cable fixed to the distal facing surface of the PCB and configured to steer a distal portion of the shaft, wherein the cable is electrically conductive.

15. The medical device of claim 14, wherein a proximal end of the cable is fixed to a steering actuator.

16. The medical device of claim 15, wherein the cable extends through an opening on the distal facing surface of the PCB and is electrically coupled to the distal facing surface of the PCB.

17. The medical device of claim 16, wherein the PCB includes a light mounted on the distal facing surface of the PCB.

18. The medical device of claim 17, wherein the opening is surrounded by conductive plating, and wherein the cable is electrically coupled to the conductive plating.

19. The medical device of claim 18, wherein the conductive plating is electrically connected to a conductive trace, which is electrically connected to the light.

20. The medical device of claim 19, wherein the cable is a first cable, wherein the opening is a first opening, the conductive plating is a first conductive plating, wherein the medical device further comprises a second cable that extends through a second opening of the PCB, wherein the second cable is electrically coupled to a second conductive plating surrounding the second opening on the distal facing surface of the PCB, wherein the first conductive plating serves as a voltage supply, and wherein the second conductive plating serves as a ground.

* * * * *